United States Patent
Sander

(10) Patent No.: US 7,423,807 B2
(45) Date of Patent: Sep. 9, 2008

(54) OPHTHALMOSCOPIC STEREOMICROSCOPE WITH CORRECTION COMPONENT

(75) Inventor: Ulrich Sander, Rebstein (CH)

(73) Assignee: Leica Microsystems (Schweiz) AG, Heerbrugg (CH)

(*) Notice: Subject to any disclaimer, the term of this patent is extended or adjusted under 35 U.S.C. 154(b) by 0 days.

(21) Appl. No.: 10/891,765

(22) Filed: Jul. 15, 2004

(65) Prior Publication Data

US 2005/0012991 A1    Jan. 20, 2005

(30) Foreign Application Priority Data

Jul. 17, 2003  (DE)  ................ 103 32 602
Jul. 17, 2003  (DE)  ................ 103 32 603

(51) Int. Cl.
    *A61B 3/13*    (2006.01)
(52) U.S. Cl. .................. 359/381; 359/377; 351/216
(58) Field of Classification Search ........ 359/380, 359/388
    See application file for complete search history.

(56) References Cited

U.S. PATENT DOCUMENTS

| | | | | |
|---|---|---|---|---|
| 4,710,000 A | * | 12/1987 | Spitznas et al. | 359/377 |
| 4,723,842 A | * | 2/1988 | Twisselmann et al. | 359/372 |
| 4,786,161 A | * | 11/1988 | Muller et al. | 351/205 |
| 4,856,872 A | | 8/1989 | Spitznas et al. | |
| 4,935,612 A | * | 6/1990 | Bierleutgeb | 250/201.2 |
| 5,002,376 A | * | 3/1991 | Hoppl et al. | 359/377 |
| 5,282,085 A | * | 1/1994 | Volkert et al. | 359/377 |
| 5,321,447 A | | 6/1994 | Sander et al. | |
| 5,438,456 A | * | 8/1995 | Grinblat | 359/835 |
| 5,442,487 A | * | 8/1995 | Mizuno | 359/784 |
| 5,925,874 A | * | 7/1999 | Liegel et al. | 250/201.3 |
| 6,212,006 B1 | * | 4/2001 | Reiner | 359/388 |
| 6,473,229 B2 | | 10/2002 | Nakamura | |
| 6,598,972 B2 | | 7/2003 | Strahle | |
| 2001/0010592 A1 | * | 8/2001 | Nakamura | 359/376 |
| 2002/0191280 A1 | * | 12/2002 | Horiguchi et al. | 359/383 |
| 2003/0165012 A1 | | 9/2003 | Strahle et al. | |
| 2004/0156017 A1 | * | 8/2004 | Sander | 351/206 |
| 2005/0012994 A1 | * | 1/2005 | Sander | 359/385 |

FOREIGN PATENT DOCUMENTS

DE    3539009 A1  *  5/1987
DE    9415219 U1     1/1995

OTHER PUBLICATIONS

Oculus Optikgerate GmbH, product brochure: SDI II BIOM II, Sep. 1998.

* cited by examiner

*Primary Examiner*—Alessandro Amari
*Assistant Examiner*—Mark Consilvio
(74) *Attorney, Agent, or Firm*—Hodgson Russ LLP

(57) ABSTRACT

Microscope, especially stereoscopic microscope, with a main objective (2), a magnification system (8, 7) disposed thereafter, and a supplementary optical system (30, 32a) for carrying out intraocular surgery, wherein the supplementary optical system comprises at least one ophthalmoscopic lens (30a) disposed before the main objective lens (2) and at least one optical component (32a) disposed behind the main objective lens (2) for providing a refraction and a focussing of a viewing beam path passing through the main objective (2), and the optical axis (12d) of the magnification system (7) disposed behind the main objective extending essentially perpendicularly to the optical axis (11) of the main objective (2).

11 Claims, 2 Drawing Sheets

OPHTHALMOSCOPIC STEREOMICROSCOPE WITH CORRECTION COMPONENT

CROSS-REFERENCE TO RELATED APPLICATIONS

The present application claims priority of German patent application numbers 103 32 603.0 and 103 32 602.2, both filed Jul. 17, 2003.

FIELD OF THE INVENTION

The present invention relates to microscopes, especially to stereoscopic microscopes of the type having a main objective, a magnification system disposed behind the main objective, and a supplementary optical system for carrying out intraocular surgery.

BACKGROUND OF THE INVENTION

Ophthalmological microscopes as such are known. They comprise a main objective, a magnification system disposed thereafter and a binocular system with eye-pieces (oculars). In order to provide a stereoscopic microscope, a splitting of a beam path passing through the main objective into a number of beam paths may be carried out in a magnification system, which may, for example, be provided as a zoom-system. Further, ophthalmological microscopes are known, which allow for a simultaneous viewing of an object by a first user (main surgeon) and a second user (assistant).

In order to carry out intraocular surgery, for example in order to microscopically view the fundus or parts of the vitreous body close to the fundus of a human eye, supplementary optical systems are needed at the stereoscopic microscopes. These consist of lenses, which are disposed in front of the main objective (on the side of the object). Since they are thus positioned outside the body of the microscope, they prove to be very disturbing for the operating surgeon, since they reduce the free working distance. Further, such supplementary optical systems are very sensitive to dirt, so that the sterility of such supplementary optical systems, which are disposed in such a way, is insufficient.

In the brochure "SDI II, BIOM II" of Oculus Optikgeräte GmbH dated 1998, as well as in U.S. Pat. No. 4,856,872, such a supplementary optical system is described. There, it may be seen that a lens system designed as a BIOM-system (BIOM: Binocoular Indirect Ophthalmomicroscope) protrudes downwards into the operation area and, for this reason, may be easily contaminated by the activity of the surgeon. Thereby, the lens, which is disposed close to the object (ophthalmoscopical lens), as well as the lens, which is disposed closer to the main objective (reduction lens) may be contaminated. In case of time consuming surgery, both lenses of this preceding supplementary optical system must be cleaned in regular intervals, which proves cumbersome.

A microscope comprising such a supplementary optical system is, for example, known from the German utility model G 94 15 219.5.

From DE 41 14 646 C2 there is known a solution, according to which an ophthalmological attachment for a surgical microscope is accommodated in an attachment housing, which is laterally positionable with respect to the main objective. The attachment comprises an ophthalmoscopical lens, an optical image erecting system and a slideable lens for focussing. The arrangement of these two lenses or lens systems in one housing is considered to be cumbersome. Also, such a housing proves to be disturbing for the surgeon in practical use.

From DE 35 28 356 A1, a device for examination and surgery of front and back eye areas is known. In this device for examination and surgery of the eye, an ophtalmological objective is combined with an operation microscope, the main objective of which is combined with an optical system of variable (frontal) focal lengths.

SUMMARY OF THE INVENTION

Therefore, an object of the invention is to provide a microscope comprising a supplementary optical system, which especially allows for intraocular surgery, and which is provided in front of (preceding) the main objective, a contamination of said supplementary optical system during surgery being substantially avoidable, the supplementary optical system being of a small overall size, thus getting in the way of or disturbing the surgeon as little as possible. The beam paths within the microscope shall be as simple as possible.

This object is solved by a microscope according to the present invention. The microscope according to the invention is provided with a supplementary optical system comprising at least one lens disposed before (preceding) the main objective, and at least one component, especially at least one lens, which is disposed behind the main objective. By means of this positioning of a part of the supplementary optical system behind the main objective, i.e. on the observer's side in the microscope housing with respect to the main objective, a contamination of this part of the supplementary optical system during surgery may be effectively avoided. According to the invention, only the comparatively small ophthalmoscopical lens, which is very easy to clean, due to its (small) size, remains on the object side of the main objective. Thereby, the cleaning effort, especially during surgery, is reducible, as compared to conventional solutions. The microscope according to the invention is further characterised in that the optical axis of the magnification system disposed behind the main objective extends substantially perpendicularly to the optical axis of the main objective. With this measure, the vertical dimensioning of the microscope, and thus the ergonomical height can be minimised in an effective way.

Advantageously, the ophthalmoscopical lens disposed before the main objective and the component disposed behind the main objective are arranged along the optical axis of the main objective. With this measure, deflections of convergent beam paths between the ophthalmoscopical lens and the main objective can be avoided, as after passing the main objective and the component disposed behind the main objective, beam paths originating from the object propagate essentially as parallel beams. For deflection of such parallel beams, relatively small deflection elements can be used, without vignetting effects occurring. The deflection of convergent beams requires relatively large deflection elements, if such vignettings are to be avoided.

It is furthermore preferred that the magnification system according to the invention comprises two, particularly three or four viewing channels. Especially, the provision of a magnification system comprising four viewing channels behind an inverter-system (i.e. on the side of the user) renders possible a simple stereoscopic viewing by two viewers, i.e. a main surgeon and an assistant. By means of such an arrangement of the magnification system behind the inverter-system it is only necessary to provide a single inverter-system for both the main surgeon and the assistant. It is also possible to position a magnification system comprising a plurality of magnification channels in front of the inverter-system (i.e. on the object side).

It is advisable that the supplementary optical system for carrying out intraocular surgery provided according to the invention is designed as a BIOM-system. Such systems apply the principles of indirect ophthalmoscopy and allow for a very wide-angle observation (inspection) for example of the fundus of the eye. In using such systems, the eye can be rolled freely, so that also the periphery of the fundus may readily be inspected.

In a preferred embodiment of the microscope according to the invention, the supplementary optical system lens disposed in front of the main objective may be removed from the viewing beam path especially by pivoting, and/or the optical component disposed behind the main objective may be removed from the viewing beam path, especially by displacement. Thus, since especially the complete supplementary optical system is removable from the viewing beam path, a microscope equipped in such a way is also useable for normal ophthalmological applications, which do not require such supplementary optical systems.

It is advantageous that the supplementary optical system component, which is disposed behind the main objective, is slideable back and forth in the direction of the viewing beam path incident thereon. With this measure, a focussing of the viewing beam path, which may be necessary due to the existence of the supplementary optical system, is possible in a simple manner. This means, for example that it is possible, by means of this lens to focus onto the area of the eye, which is of interest, without having to effect changes to the surgical microscope itself.

It is advantageous that a deflection element is provided, which deflects a beam path propagating along the optical axis of the main objective into a first microscope plane extending substantially perpendicularly to the optical axis of the main objective.

According to a further preferred embodiment, two deflection elements are provided, by means of which a beam path propagating in the first microscope plane can be deflected into a second microscope plane, at least one of these deflection elements being provided with a focal power. Such deflection elements provided with a focal power can provide an inverter-system in a simple and cost-effective manner. The first and second microscope planes advantageously extend substantially horizontally.

According to a further preferred embodiment of the microscope according to the invention, a deflector element is disposed between the main objective and the component of the supplementary optical system disposed behind the main objective, so that the beam path passes through the component of the supplementary optical system, which is disposed behind the main objective, at an angle, especially perpendicular to the beam path through the lens of the supplementary optical system disposed in front of the main objective. By means of this measure, it is possible, for example, to insert the component of the supplementary optical system, which is disposed behind the main objective, into a substantially horizontally extending beam path, whereby the overall height of the microscope may be kept very small.

According to a further preferred embodiment of the microscope it is intended to provide the deflector element, which is disposed between the main objective and the optical component of the supplementary optical system disposed behind the main objective with a focal power. By means of this measure, it is possible to transfer the focal power to be provided by the component disposed behind the main objective at least partly to the deflector element. Thereby, greater freedom is obtained for the design of the optical component disposed behind the main objective lens. It is advisable to design the deflector element as a concave mirror or as a prism comprising accordingly curved surfaces. The deflector elements for deflecting the beam path from the first into the second plane of the microscope may also be provided with a focal power, as already mentioned.

According to a further preferred embodiment of the inventive microscope, there is provided an electromechanical connection between the ophthalmoscopical lens and the optical component of the supplementary optical system disposed behind the main objective, in order to jointly pivot out or displace these components. In this context, it is possible, for example, to provide each of the components with an electric motor the two electric motors being controllable jointly or interdependently.

It is advisable to choose the refractive (focal) power and the range of displacement of the optical component disposed behind the main objective in such a way that a focussing compensation is possible from the position of observation of the object, if the ophthalmoscopical lens is not used, up to the position of the intermediate image that results from the use of the ophthalmoscopical lens. With this measure, it can be ensured that no displacement of the microscope body is necessary during the focussing onto an object, since this focussing may be achieved merely by displacement of the optical component disposed behind the main objective.

It is further preferred to provide the microscope according to the invention with an autofocus system. By means of such an autofocus system, the displacement of the optical component disposed behind the main objective lens parallel to the optical axis of the main objective lens may be controlled in a simple manner. Autofocus systems as such are known. For example, an autofocussing occurs by coupling a laser beam according to the triangulation principle.

BRIEF DESCRIPTION OF THE DRAWINGS

The invention will now be further described with reference to the accompanying drawings, in which.

DETAILED DESCRIPTION OF THE INVENTION

Figure 1:
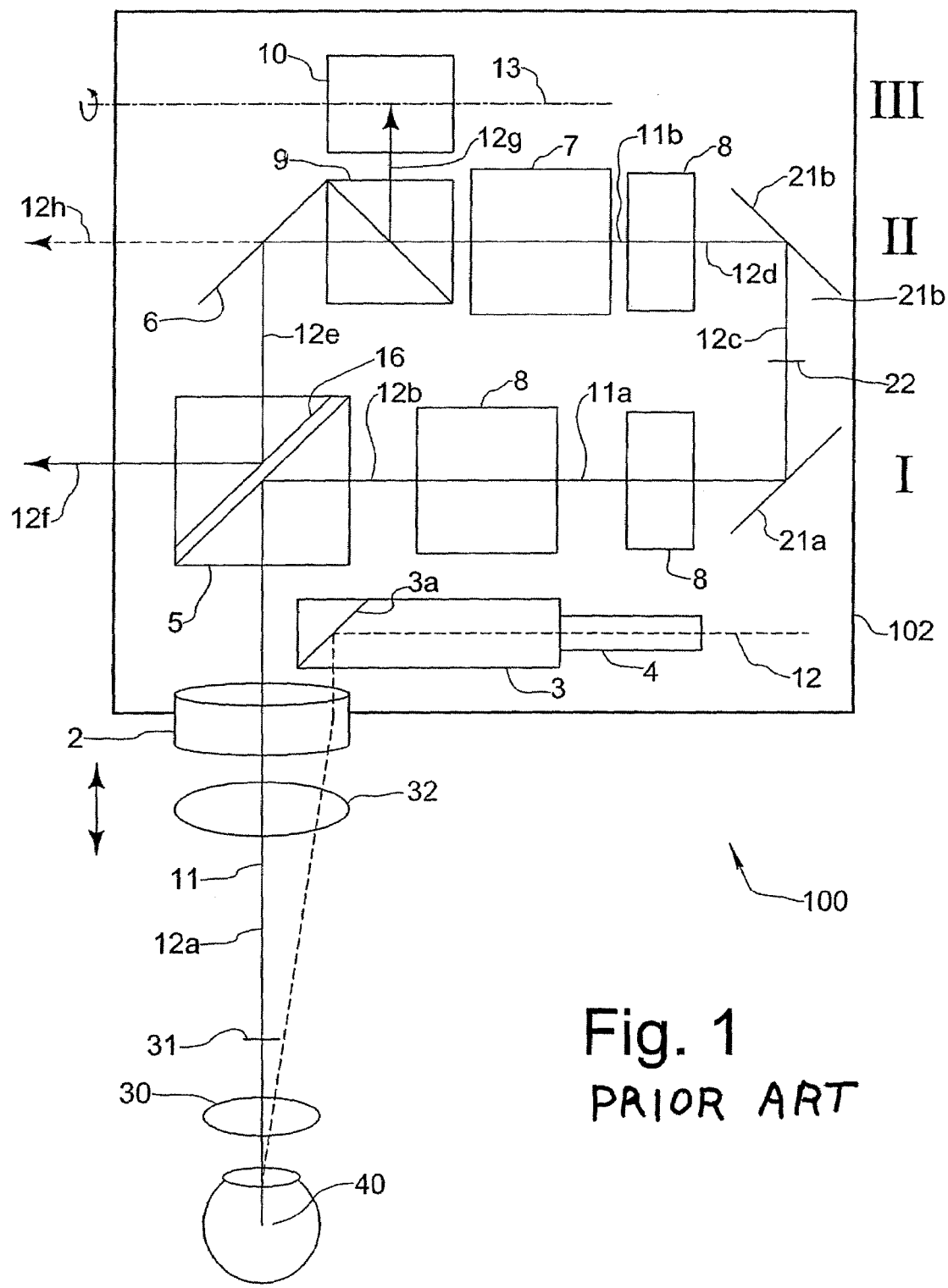
FIG. 1 shows a schematic lateral sectional view of a microscope provided with a prior art supplementary optical system for carrying out intraocular surgery.

A stereoscopic microscope with a conventional supplementary optical system for carrying out intraocular surgery is referred to as a whole by reference numeral 100 in FIG. 1. The stereoscopic microscope has a microscope body 102, in which a main objective 2 and a magnification system 7, especially provided as a zoom-system, are disposed as main optical components.

The microscope 100 further comprises deflector elements 5, 21a, 21b provided as plane mirrors. By means of these deflector elements, viewing beams 12a-12h, which emerge from an object 40 to be inspected, and which at first proceed substantially (at 12a) in a vertical direction through the main objective 2 along the optical axis 11 thereof, are deflectable into two substantially horizontally extending planes I, II of the microscope (at 12b, 12d). It can be seen that the magnification system 7 in the shown embodiment is disposed in the second plane II.

At the object side of the magnification system 7, selectively in the first and/or second plane I, II, additional optical system components are provided, here generally referred to by 8, as for example filters, laser shutters, optical splitters (dividers) or SDI-devices (stereoscopic diagonal inverter).

The microscope 100 shown is designed for simultaneous viewing of the object 40 by a main surgeon and an assistant. To this end, in the second plane II of the microscope, a deflector element or a decoupling means 9, is provided, which causes the decoupling of the viewing beam path 12g for the assistant with respect to the viewing beam path 12d for the main surgeon. The viewing of the object 40 by the assistant takes place in a third plane III of the microscope, as is further described below.

The stereoscopic splitting of the homogeneous beam path 12a, which is incident upon the main objective 2, may take place at an arbitrary position inside the microscope housing 102 in a known manner. It is advisable that the stereoscopic splitting takes place by means of the magnification system 7, which may, for example, comprise two or four stereoscopic viewing channels. It is preferred to provide the magnification system 7 with four stereoscopic viewing channels grouped in pairs, wherein one pair of stereoscopic viewing channels is provided for the main surgeon and one pair is provided for the assistant, respectively. The provision of four magnification channels in connection with the magnification system provides for a small vertical distance between the respective viewing axis and the object to be viewed, this for the main surgeon as well as for the assistant. It is advisable that two magnification channels of the magnification system, especially the magnification channels for the main surgeon, proceed horizontally at the same height, whereas two further magnification channels proceed parallel hereto, i.e. also horizontally, with a vertical spacing to one another. These vertically spaced magnification channels are especially useable for the assistant. In this respect, it is especially possible that the vertically spaced magnification channels extend above or below, respectively, the center of the connecting line between the magnification channels for the main surgeon, which are provided at the same height. Thereby, an especially dense packaging of the four magnification channels is given, whereby an especially small overall height of the stereoscopic microscope according to the invention may be obtained. For reasons of clarity, in FIGS. 1 and 2 only single viewing beam paths are shown. In particular, the viewing beam path in the second plane II of the microscope is referred to by 12d. It should be noted that the two viewing beam paths for the main surgeon are positioned behind one another, when viewed in the direction of sight in FIGS. 1 and 2, so that only one of these viewing beam paths can be shown. The viewing beam paths in the second plane of the microscope, which have a vertical spacing to one another, and which, by the deflector element 9, are deflected into the third plane III of the microscope, are not shown in detail. The vertically proceeding viewing beam path 12g, with respect to the preferred embodiment of the magnification system 7, is merely a schematic simplification, since in reality in this embodiment, in the illustration of the FIGS. 1 and 2, two adjacent vertically proceeding viewing beam paths are deflected into the third plane of the microscope. A complete illustration of this preferred embodiment of a magnification system is disclosed in DE 102 55 960, to which reference is made herewith.

By means of binocular tubes (not shown), which are provided following the decoupling means 9, a stereoscopic viewing of object 40 is possible by the main surgeon and/or by the assistant.

It is advisable that in order to obtain a further deflection of the stereoscopic viewing beam paths for the main surgeon, a further deflector element 6 is provided behind the decoupling means 9, by means of which the viewing beam paths (at 12e) for the main surgeon are deflectable from the second plane II of the microscope back into the first plane I of the microscope, for example. A further deflector element 16 is provided in the first plane I of the microscope, by means of which the viewing beam paths for the main surgeon are substantially deflected back into a horizontal direction. The beam paths to a binocular tube (not shown) in plane I of the microscope are referred to by 12f.

If, however, a viewing of object 40 by the main surgeon is desired in the second plane II of the microscope, deflector element 6 may be omitted, or it may be designed to be slideable out of the beam path or it may be designed to be semitransparent. In this case, for the main surgeon the viewing beam paths referred to by 12h are produced.

For the assistant, a further deflector element 10 is provided in the third plane III of the microscope, by means of which the beam paths decoupled by decoupling means 9 are deflectable into the third plane of the microscope (i.e. substantially in a horizontal direction).

Depending on the orientation of the assistant beam paths, it is advisable to be able to pivot the deflector element 10 about an axis 13 or about an axis extending perpendicular to this axis, so that a viewing by the assistant by means of the assistant binocular tube (not shown) is possible, in the example shown in a direction into the drawing plane, or out of the drawing plane.

An illumination system of the shown microscope is as a whole referred to by 3, 4, wherein 4 refers to a fiber cable for an illumination device 3. By means of a deflector element 3a, light from the fiber cable is supplied to the object 40, which is to be illuminated, at a desired angle.

Microscope 100 is further provided with a supplementary optical system 30, 32, which makes it possible to carry out intraocular surgery.

The supplementary optical system comprises an ophthalmoscopical lens or fundus lens 30 and a correcting lens 32. The ophthalmoscopical lens 30 serves to compensate the refractive power of the eye.

Since the ophthalmoscopical lens 30 and the correcting lens 32 are used together in intraocular surgery, by means of a pivoting mechanism (not shown), they may functionally be pivoted out of the beam path 12a between object 40 and main objective 2, i.e. the optical axis 11 of the main objective 2.

By means of this pivotability, it is ensured that the microscope 100 may also be used for other surgical interventions, which do not require such a supplementary optical system.

With respect to the operation of the supplementary optical system, it should be noted that the ophthamoscopical lens 30 creates a first intermediate image 31 of the object 40 in front (before) of the main objective 2 of the microscope 100. The image 31 created by the ophthalmoscopical lens 30 is vertically and laterally reversed. It is advisable that the correcting lens 32 is designed to be slideable along the optical axis 11, as is indicated by a double sided arrow. By means of sliding the correcting lens 32, it is possible, for example, to focus onto a section of interest of the object or eye 40, without having to accomplish adjustments on the optical systems inside housing 102.

Since the intermediate image 31 is laterally reversed and vertically reversed, and therefore pseudo-stereoscopic in viewing, the additional components 8 comprise SDI-elements, which correct this effect. Such SDI-elements consist of a relatively complex set of prisms. Systems of this kind as such are known, and do not require further explanation at this point, because they are not essential for the invention.

By means of a lens imaging, it is also possible to transform such a laterally and vertically reversed and pseudo-stereoscopic image back into a laterally correct and vertically correct image. However, such a lens optical system, which has to consist of at least two lenses, shows a relatively long overall length.

A preferred embodiment of the microscope according to the invention will now be explained with reference to FIG. 2.

Figure 2:
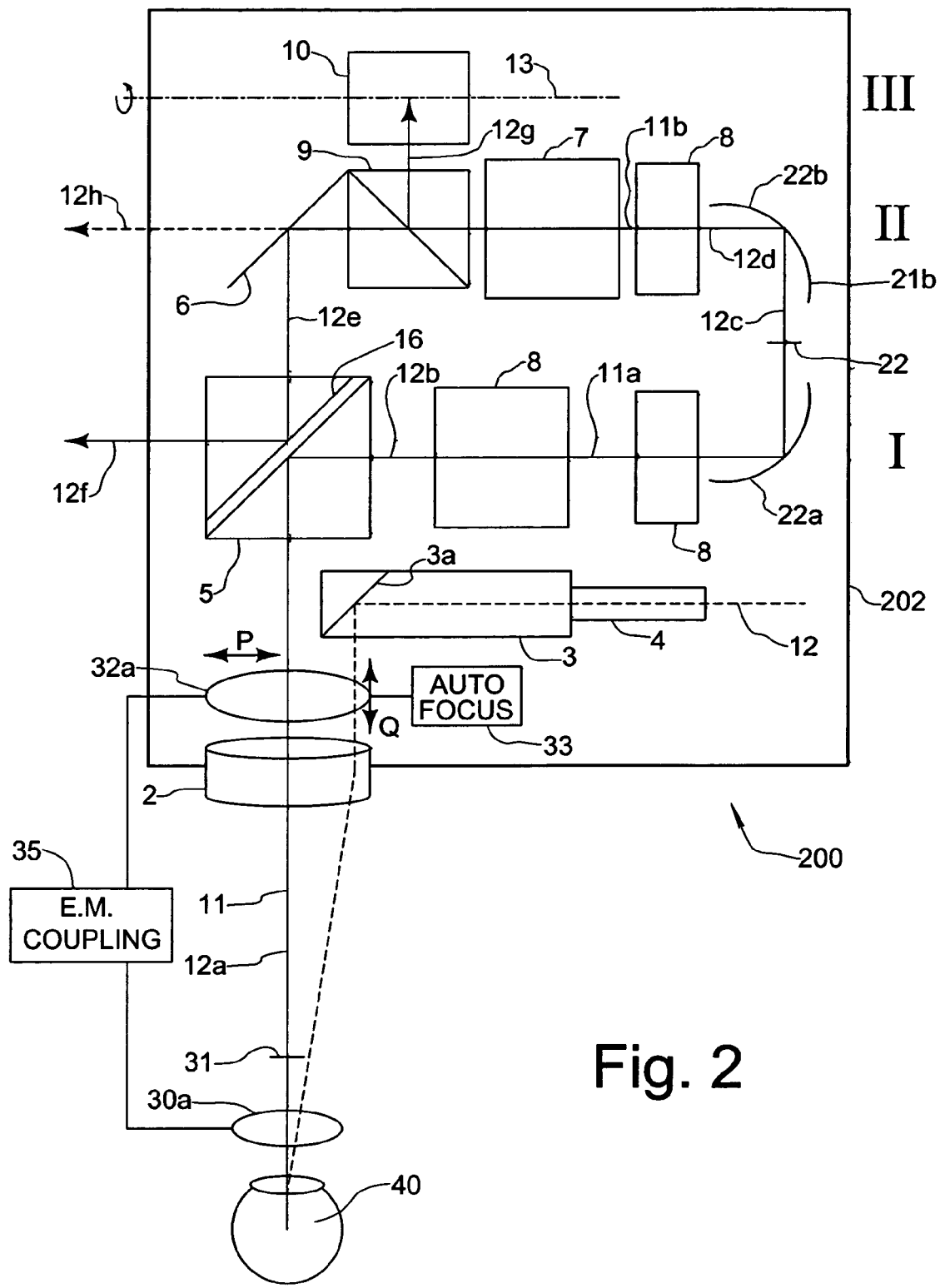
FIG. 2 shows a preferred embodiment of the inventive microscope in a view similar to that of FIG. 1.

The microscope according to FIG. 2, which as a whole is referred to by 200, differs from the microscope 100 according to FIG. 1 only in the supplementary optical system as well as the provision of the deflector elements for deflecting the beam paths from a first microscope plane I into a second microscope plane II. The further components of the microscope comply with those according to microscope 100 of FIG. 1, and therefore are referred to by the same reference signs. Therefore, a detailed description of these components and of the beam paths implemented in the microscope is omitted.

First of all, it can be seen that the ophthalmoscopical lens 30a is disposed in front of the main objective 2, as is the case in the microscope according to FIG. 1. However, a correcting lens, here referred to by 32a, is disposed behind the main objective 2, i.e. it is positioned inside the housing 202 of the microscope. The correcting lens 32a is removable from the viewing beam path 12a, which passes through the main objective 2, as is indicated by the double-sided arrow P. Further, the correcting lens 32a is slideable along the optical axis 11 of the main objective 2 and the viewing beam path 12a, as is indicated by the double-sided arrow Q. The ability to remove the correcting lens 32a allows for the use of the microscope 200 for arbitrary ophthalmological applications, when the fundus lens (ophthalmoscopical lens) 30a is pivoted out of or removed from the viewing beam path through the main objective lens 2. The slideability of the correcting lens 32a parallel to the optical axis 11 allows for a focusing of the beam path 12a incident upon the main objective 2. Preferably, an autofocus system 33, indicated schematically in FIG. 2, is provided to automatically move correcting lens 32a in axial directions Q to achieve focusing.

According to the invention, in that the correction lens 32a now is positioned within the housing 202 of the microscope, a contamination during surgery can be prevented. According to the invention, the only lens that is still subject to the danger of contamination during surgery is the ophthalmoscopical lens 30a, which, however, may be cleaned or exchanged easily without considerable effort due to its small size.

As already indicated, the correcting lens 32a serves to focus the viewing beam path penetrating the main objective 2 onto the intermediate image 31. According to a further embodiment of the microscope 200, which is not shown, it is possible to omit correcting lens 32a, and to realize the respective refracting power as well as the focussing ability within or by means of the additional optical system components 8.

It is advisable that an optical element of the additional optical system components 8, for example a lens, is designed pivotally or relocatably, with respect to the optical axis of the first plane I or the second plane II of the microscope, which are referred to by 11a, 11b herein. By means of a respective slideability, a focussing is possible here as well. By means of this solution, in which the function of the correcting lens 32a is implemented by means of an optical component in the context of the additional optical system components 8, the overall height of the microscope may be reduced, as the optical axis of the additional components 8 extends in the horizontal plane I or II.

Furthermore, it is possible to implement a dividing of the functions of the correcting lens 32a, i.e. the provision of the refractive power and of the focussing among several lenses. For example, it can be considered to provide the lens 32a at the position shown in FIG. 2, in a non-moveable manner with respect to optical axis 11. Such a lens only fulfils the function of providing the refractive, power. The focussing may then be implemented within the context of the additional optical system components 8 by means of respective slideability of a lens along the optical axis 11a in the first plane I or the optical axis 11b in the second plane II. It might further be considered to provide deflector element 5 with a focal power. This is possible, for example, in that the deflector element is provided in form of a concave mirror or by means of a prism comprising curved surfaces (not explicitly shown in FIG. 2).

It is further to be noted that it is also possible to provide the deflection element 5 between the main objective 2 and the component 32a disposed behind the main objective. This leads to an arrangement of the optical component 32a in the first microscope plane I or along the optical axis 11a. This embodiment is not explicitly shown in FIG. 2.

Moreover, deflector elements designated 22a, 22b in FIG. 2 are preferably implementable as concave mirrors or prisms comprising curved surfaces. By means of this measure, it is possible, for example to create an intermediate image 22 along the vertically proceeding beam path 12c between the planes I, II of the microscope. Thus, this vertically proceeding section may be used to optically modify the beam path, whereby the horizontal extension of the microscope 200 may be reduced. Especially, as mentioned, the intermediate image 31 behind the ophtalmoscopical lens 30a is laterally inverted and vertically (height) inverted and thus pseudo-stereoscopic in viewing. The deflection elements 22a, 22b are capable of generating an image correct in its vertical (height) and lateral extensions out of this pseudo-stereoscopic image, i.e. to function as an inverter. In particular, the following propagation of the viewing beam path results: by means of the correcting or auxiliary lens 32a, or, if applicable (subsequent to deflecting by deflecting element 5) of the additional optical components 8, the beam paths, which result from the vertical and laterally reversed intermediate image 31 are converted into a beam path, which is substantially parallel to the axis along the optical axis 11b of the first plane I of the microscope. This beam path parallel to the axis is by means of concave mirror 22a, deflected into a further intermediate image 22 in the vertical beam path 12c between the two planes I, II of the microscope. This intermediate image 22 is laterally correct and vertically correct, i.e. stereoscopic. By means of the concave mirror 22b, this intermediate image 22 is imaged to infinity in the second plane II of the microscope again (the beam path being substantially parallel to the axis). The magnification system 7 is preferably designed as a four-channel zoom system along the third optical axis 11d, whereby, as already mentioned, the stereoscopic splitting for the main surgeon and the assistant is effected. The double functionality of the deflector elements 22a, 22b should once again be noted. On the one hand, they serve to deflect the beam paths and thereby to optimally exploit the space inside the microscope body 202, on the other hand, they serve to invert a pseudo-stereoscopic intermediate image, whereby the number of optical components is reduced, as compared to conventional solutions.

Therefore, the deflector elements 22a, 22b both serve to deflect the respective viewing beam paths inside the body of the microscope, as well as to create an image or image to infinity, respectively, whereby an image erection of an inverted, pseudo-stereoscopic intermediate image is provided in a simple and cost-effective manner.

Therefore, according to the invention, it is possible to replace conventionally used SDI-systems, which comprise relatively complex prism systems and plane mirror systems, by simple concave mirrors 22a, 22b. It is also possible to provide the double functionality provided by the concave mirrors 22a, 22b by means of deflector prisms provided with a refractive (focal) power. Instead of deflector elements 22a or 22b, it might also be considered to provide deflector element 5 with a focal power. Thereby, the inverted intermediate image would be created in the first plane I of the microscope.

By positioning a magnification system comprising four viewing channels behind the deflection elements 22a, 22b provided as concave mirrors, it is possible to provide stereoscopic viewing for the main surgeon and the assistant, only one inverter-system, provided by the deflection elements 22a, 22b being necessary. The provision of only one inverter-system for the main surgeon and the assistant can also be achieved if the magnification system is arranged in front of the inverter-system (i.e. on the object side). It must, however, be provided before the decoupling device (designated 9 in FIG. 2), by means of which the beam paths for the main surgeon and the assistant are deflected in different directions.

According to the invention, all optical components together are provided within the microscope body 202, with the exception of the ophthalmoscopical lens 30a. This lens 30a, as explained, is mechanically coupled to the microscope and pivotally held, as well as electromechanically connected to the correcting lens 32a by an electromechanical coupling 35 indicated schematically in FIG. 2. Electromechanical coupling 35 is preferably provided in order to jointly move the ophthalmoscopical lens and the optical component with respect to the optical axis of the main objective.

For the reason of completeness, it should finally be noted that it is possible to provide a means for introducing (coupling in) data, for example at the position of the deflector element 6 or at another suitable location. Here, for example an optical beam divider may be provided, for example for a documentation device.

With respect to the illumination means 3, it is finally noted that according to the embodiments shown, the illumination is introduced between the correction lens 32, 32a and the magnification system 7. This leads to the advantageous effect that the illumination field always has the proper size (proper diameter) with respect to a focussing set by means of the correction lens 32, 32a.

List of Reference Signs:
- 2 main objective
- 3 illumination means
- 3a deflector element
- 4 fiber optic cable
- 5,6 deflector elements
- 7 magnification system (zoom system)
- 8 optical components
- 9 deflector elements (decoupling means)
- 10 deflector element
- 11 optical axis of the main objective 2
- 11a, 11b optical axis of the first or second plane of the microscope, respectively
- 12a-12h viewing beam paths
- 13 pivoting axis of deflector element 10
- 16 deflector element
- 21a, 21b deflector elements
- 22a, 22b deflector elements (concave mirrors, inverter-system)
- 22 intermediate image
- 30 ophthalmoscopical lens (fundus lens)
- 3a ophthalmoscopical lens (fundus lens)
- 31 Intermediate image
- 32 correcting lens
- 32a correcting lens
- 40 Object
- 100 stereoscopic microscope
- 102 Housing
- 200 stereoscopic microscope
- I, II, III planes of the microscope
- 33 autofocus system
- 35 electromechanical coupling

What is claimed is:

1. A microscope comprising:
a main objective having an optical axis, the main objective being focused at an object plane corresponding to a front portion of a patient's eye during non-intraocular ophthalmic surgery;
a supplementary optical system supplemental to the main objective for carrying out intraocular ophthalmic surgery, the supplementary optical system including an ophthalmoscopical lens located before the main objective externally from a housing of the microscope and a correction component located after the main objective internally within the housing of the microscope;
wherein the externally located ophthalmoscopical lens and the internally located correction component are inserted together into the optical axis during intraocular ophthalmic surgery and removed together from the optical axis during non-intraocular ophthalmic surgery;
wherein the ophthalmoscopical lens forms an intermediate image at a plane located between the ophthalmoscopical lens and the main objective, and the correction component reduces the focal length of the microscope to focus at the intermediate image plane without focus adjustment of the main objective, the correction component being independently movable along the optical axis relative to the main objective; and
a magnification system after the ophthalmoscopical lens, the main objective and the correction component, the magnification system having an optical axis extending substantially perpendicularly to the optical axis of the main objective.

2. The microscope according to claim 1, wherein the magnification system includes at least two viewing channels.

3. The microscope according to claim 1, wherein the ophthalmoscopical lens is removable from the optical axis of the main objective by pivoting the ophthalmoscopical lens out of the optical axis of the main objective.

4. The microscope according to claim 1, wherein the correction component is removable from the optical axis of the main objective by moving the correction component laterally out of the optical axis of the main objective.

5. The microscope according to claim 1, further comprising a deflection element for deflecting a beam propagating along the optical axis of the main objective into a first microscope plane extending substantially perpendicularly to the optical axis of the main objective.

6. The microscope according to claim 5, further comprising two deflection elements for deflecting a beam propagating in the first microscope plane such that the beam propagates in a second microscope plane, wherein at least one of the two deflection elements has a focal power.

7. The microscope according to claim 5, wherein the deflection element is located between the main objective and the optical component of the supplementary optical system.

8. The microscope according to claim 5, wherein the deflection element has a focal power.

9. The microscope according to claim 1, wherein the ophthalmoscopical lens and the correction component are electromechanically coupled to each other in order to jointly insert and remove the ophthalmoscopical lens and the correction component with respect to the optical axis of the main objective.

10. The microscope according to claim 1, characterized in that a refractive power and an axial displacement range of the optical component are such that a focusing correction is possible from a position of the viewing of the object if the ophthalmological lens is not used to a position of an intermediate image resulting if the ophthalmological lens is used.

11. The microscope according to claim 1, further comprising an autofocus system for controlling the position of the optical component in a direction parallel to or coincident with the optical axis of the main objective.

* * * * *